United States Patent [19]

McCoy et al.

[11] 3,932,460

[45] Jan. 13, 1976

[54] METHOD FOR THE PREPARATION OF A TETRAALKYL-TETRAOXA-UNDECANE

[75] Inventors: David R. McCoy, Wappingers Falls; Terence B. Jordan, Fishkill; Frank K. Ward, Hopewell Junction, all of N.Y.

[73] Assignee: Texaco Inc., New York, N.Y.

[22] Filed: June 27, 1974

[21] Appl. No.: 483,600

[52] U.S. Cl. ............................................ 260/340.7
[51] Int. Cl.² ...................................... C07D 319/06
[58] Field of Search ................................ 260/340.7

[56] References Cited

UNITED STATES PATENTS 2,691,026   10/1954   Harvey .............................. 260/340.7

*Primary Examiner*—Anton H. Sutto
*Attorney, Agent, or Firm*—T. H. Whaley; C. G. Ries; James F. Young

[57] ABSTRACT

Method of preparing a tetraalkyl-tetraoxaundecane by the reaction of a $C_{10} - C_{16}$ aliphatic ketone with pentaerythritol in the presence of an active acid catalyst in an inert solvent at 120°–150°C. for 8 to 70 hours.

7 Claims, No Drawings

METHOD FOR THE PREPARATION OF A TETRAALKYL-TETRAOXA-UNDECANE

The present invention is directed to the preparation of a 3,3,9,9-tetraalkyl-2,4,8,10-tetraoxa [5.5] undecane wherein each alkyl group thereof contains from about one to about 14 carbon atoms with a total of from 18 to 30 carbon atoms in the four alkyl groups. The expression "said undecane" as used hereinafter is meant to refer to the above compound.

These tetraalkyl tetraoxaundecanes have utility as synthetic lubricating oil base stocks, where the bulk oil temperature in use is below about 300°F. and the skin temperature is below about 550°F.

It is known that aldehydes and simple ketones such as acetone and cyclohexanone form cyclic di-acetals and diketals respectively, with pentaerythritol under relatively mild conditions such as temperatures below about 100°C. and acidic catalysts such as HCl, $ZnCl_2$ and sulfonic acid cation exchange resins. However, the preparation of diketals from pentaerythritol with relatively high molecular ketones has not been taught heretofore.

It has now been found that said undecanes can be prepared in good yields by a novel method which comprises reacting a $C_{10} - C_{16}$ dialkyl ketone containing from about one to 14 carbon atoms therein per alkyl group with pentaerythritol in a prescribed mole ratio of 2 to 4 moles of said ketone per mole of said pentaerythritol, in the presence of a reaction catalyst selected from the group consisting of organic sulfonic acids, preferably para-toluenesulfonic acid, which is used in an amount of 1 to 10% by weight, based on pentaerythritol, in the presence of an inert organic solvent with a boiling point above 110°C., preferably xylene or chlorobenzene, in an amount of 20 to 80% by volume, of the total reaction mixture, at a reaction temperature between 120° and 150°C., for 8 to 70 hours, while optionally maintaining a blanket of an inert gas over said reactants, and removing water of reaction by azeotropic distillation, and thereafter recovering the formed said undecane from the resulting reaction products.

The ketone component used in the preparation of said undecane is an aliphatic ketone of the type

containing from about one to 14 carbon atoms therein in each alkyl group. Suitable ketones may be the symmetric or asymmetric ketones of varying carbon number within the above range. A particularly preferred group of ketones consists of $C_{10} - C_{16}$ ketones prepared by the dehydrogenation of the corresponding secondary alkanols obtained by the boric acid-catalyzed air oxidation of linear hydrocarbon mixtures.

Representative ketones include the following species: dipentyl-, disopentyl-, dihexyl-, methyl nonyl-, methyl undecyl-, ethyl undecyl-, including mixtures of mixed ketones.

The pentaerythritol component of the starting reaction mixture is more properly referred to as 2,2 bishydroxymethyl- 1,3-propanediol, but the former term is used herein for brevity.

It has been found that most satisfactory results are obtained using mole ratios of 2 to 4 moles of ketone per mole of pentaerythritol.

The acidic catalyst required in the method of the present invention is an active acid catalyst, an organic sulfonic acid, such as p-toluene sulfonic acid.

The acidic catalyst is used in an amount of from about 1 to 10% by weight, based on pentaerythritol, preferably in amounts between 1 and 2% by weight for best results.

The solvent component of the reaction mixture is one in which the reactants and catalyst are substantially soluble and, in addition, which has a boiling point high enough to permit reaction temperatures at atmospheric pressure of at least 120°C. but below 200°C. to permit ready separation from the resulting reaction products.

Suitable solvents include xylene and chlorobenzene, although the latter results in decreased product yields. Other inert organic solvents can be used if they are capable of forming an azeotrope with water and preferably boil in the range of 120° to 150°C.

Solvents that are not satisfactory include benzene, toluene, trichlorobenzene, dimethylformamide, ethanol, mixtures of dimethylformamide and benzene (1/1, 2/1, by volume), and benzene and nitromethane (1/1) as no said undecane is formed with these solvents.

The preferred solvent is xylene and is generally employed in an amount of about 50% by volume of the total reaction mixture.

It is preferred that the temperature be maintained at reflux conditions to aid in removal of water of reaction and to permit formation of the said undecane product. It has been found that temperatures between about 130° to about 145°C. are most suitable for temperatures lower than about 120°C., e.g. 50°-110°C., do not permit the formation of the desired product in good yields, and higher temperatures lead to product decomposition and side product formation.

Further, it is necessary to carry out the reaction for an extended period of time e.g. from about 15 to about 65 hours at the preferred temperature range of 130°-140°C. to obtain high yields of desired product, 65-86%.

The reactants are preferably blanketed by an inert gaseous atmosphere during the reaction period to minimize undesirable side reactions. Use of nitrogen gas has been found satisfactory.

Following is a description by way of example of a method of preparing the said undecane.

EXAMPLE I 0.52 mole of a $C_{12} - C_{13}$ ketone (prepared by the catalytic dehydrogenation of a boric acid-directed air-oxidation of $C_{12} - C_{13}$ n-paraffin mixture) having an average molecular weight of 192 was charged into a 500 ml round bottom flask with 4 grams p-toluene-sulfonic acid, 150 ml xylene, and 0.26 mole of pentaerythritol. The mixture was blanketed with nitrogen and heated to reflux (140°C.) with stirring. The stirred mixture was refluxed for 20 hours while removing water formed in a Dean-Stark trap. Thereafter the reaction products were cooled to room temperature. The xylene solvent was stripped therefrom and the residue was dissolved in pentane.

The product was treated with dilute sodium hydroxide to neutralize the catalyst and the organic layer was washed with water to remove pentaerythritol and inorganics. The residue was vacuum stripped to remove pentane and unreacted ketone, leaving a 78 mole % yield of said undecane. The said undecane product was positively identified by infrared spectroscopy (absence of C=O and O—H adsorptions), Molecular Weight, Found 422, (466 Theory) and elemental analysis, Found 73.5%C, 11.6%—H; (74.2%C, 12.0%—H, Theory).

EXAMPLE II

The procedure of Example I was repeated with the following variations:
0.4 mole of a $C_{10} - C_{13}$ ketone,
2 grams of acid catalyst, 65 hrs. reaction time, 68% product yield.

EXAMPLE III

The product of Example I was repeated with the following variations:
0.54 mole of a $C_{11} - C_{13}$ ketone, monochlorobenzene solvent
2 grams of acid catalyst, 65 hrs. at 132°C, 50% product yield.

EXAMPLE IV

The procedure of Example I was repeated with the following variations:
0.54 mole of a $C_{11} - C_{13}$ ketone, 16 hrs. reaction time, 86% product yield.

COMPARATIVE EXAMPLE A

The procedure of Example I was repeated using 0.4 mole of $C_{11} - C_{14}$ ketone, 0.25 mole of pentaerythritol, 2 grams of acid catalyst, benzene solvent, and 80°C reaction temperature. The yield was 0% of the desired product.

COMPARATIVE EXAMPLE B

Comparative Example A was repeated using toluene solvent and a reaction temperature of 110°C. The yield of desired product was 0%.

COMPARATIVE EXAMPLE C

The procedure of Example I was repeated with the following variations:
0.54 mole of a $C_{11} - C_{13}$ ketone, trichlorobenzene solvent,
10 hours at 213°C. The desired product yield was 0%.

Evaluation of the physical properties of the said undecane products of the method of this invention indicates they have utility as synthetic lubricating oil base stocks.

The data on the following Table show some of the bench test data obtained on the product prepared by the method of Example I above.

Table I

| | |
|---|---|
| Viscosity at 100°F., SUS | 378 |
| 210°F., SUS | 56 |
| 300°F., SUS | 37.2 |
| Viscosity Index | 93 |
| Flash Pt. COC°F., | 440 |
| Fire Pt. COC°F., | 450 |
| Pour, °F. | −57.5 |
| Hydrolytic Stability Test | |
| Rolls Royce No. 1006 (48 hr.) | |
| Neutralization No. | 0.25 |

The said undecane product of the present invention is responsive to the addition of standard methacrylate Viscosity Index Improvers to vary its viscosity properties.

The said undecane of Example I above was further evaluated to determine its corrosion properties and wear resistance.

Table II

| Said Undecane of Example I | |
|---|---|
| Copper Strip corrosion at 212°F., 3 hrs. (ASTM D130) | 1 b rating |
| Lead Strip Corrosion | −0.0074 |
| 4-Ball Test at 10 kg. load, 1 hr. 300°F., 600 rpm. | |
| Wear | 0.40 mm. scar |
| Coefficient of Friction | Max.$\mu_{10}$ 0.108 Final Av$\mu_{10}$ 0.097 |
| British Thermal Stability | Terminated at 540°F. Due to violent refluxing of fluid. |
| MacCoull Corrosion | Terminated at 8 hrs. excessive thickening |

The above data show that the said undecane has generally satisfactory corrosion and wear properties. The adverse results obtained in the British Thermal Stability Test showed it to be unsuitable at high service temperatures in the region of 500°–550°F.

The MacCoull Corrosion results show this compound is not oxidative stable. However, the addition of 0.6 wt. % of a commercially available zinc dialkyl-dithiophosphate oxidation-corrosion inhibitor thereto resulted in a bearing loss of only 17 mg. after 10 hours in this test. These results show that the said undecane can be effectively inhibited by addition of an oxidation-corrosion inhibitor.

We claim:

1. A method of preparing a 3,3,9,9,-tetraalkyl-2,4,8,10-tetraoxa [5.5] undecane wherein each alkyl group contains from one to about 14 carbon atoms therein and the total number of carbon atoms in the four alkyl groups is in the range of 18 to 30, which consists essentially of reacting from 2 to 4 moles of a $C_{10}-C_{16}$ aliphatic ketone per mole of pentaerythritol in the presence of para-toluene sulfonic acid catalyst in a reaction solvent selected from the group consisting of xylene and monochlorobenzene at a temperature in the range of from about 120°C. to about 150°C., for a reaction period of from avout 7 to 70 hours while removing water of formation by azeotropic distillation and thereafter recovering said formed tetraalkyl-tetraoxaundecane from the resulting reaction products.

2. Method as claimed in claim 1 wherein said aliphatic ketone is a mixed $C_{12} - C_{13}$ ketone.

3. Method as claimed in claim 1 wherein the mole ratio of said ketone to said pentaerythritol is 2 to 1.

4. Method as claimed in claim 1 wherein said solvent is xylene.

5. Method as claimed in claim 1 wherein said reaction temperature is 130° to 145°C.

6. Method as claimed in claim 1 wherein the reaction time is between 15 and 65 hours.

7. Method as claimed in claim 1 wherein there is maintained a blanket of an inert gaseous atmosphere over the reactants and reaction products.

* * * * *